United States Patent [19]
Takahashi et al.

[11] Patent Number: 5,899,852
[45] Date of Patent: May 4, 1999

[54] ENDOSCOPE SYSTEM WITH OPERATION INVALIDATING DEVICE

[75] Inventors: Tadashi Takahashi; Masaaki Nakasima, both of Tokyo, Japan

[73] Assignee: Asahi Kogaku Kogyo Kabushiki Kaisha, Tokyo, Japan

[21] Appl. No.: 08/807,989

[22] Filed: Mar. 3, 1997

[30] Foreign Application Priority Data

Mar. 7, 1996 [JP] Japan ............................ 8-50225

[51] Int. Cl.⁶ ..................................... A61B 1/045
[52] U.S. Cl. ................................. 600/118; 600/160
[58] Field of Search .................... 600/101, 118, 600/160, 178; 396/14, 17; 200/43.01; 361/72; 362/85, 802

[56] References Cited

U.S. PATENT DOCUMENTS

| | | | |
|---|---|---|---|
| 4,674,053 | 6/1987 | Bannai et al. | 364/476 |
| 4,723,207 | 2/1988 | Isobe et al. | 364/171 |
| 5,159,380 | 10/1992 | Furuya et al. | 600/178 |
| 5,347,994 | 9/1994 | Takahashi et al. | 600/109 |

*Primary Examiner*—John P. Leubecker
*Attorney, Agent, or Firm*—Kane, Dalsimer, Sullivan, Kurucz, Levy, Eisele and Richard, LLP

[57] ABSTRACT

An endoscope system includes an operation invalidating device which invalidates the operation of a switch or key which is actuated to control the operation of a device connected to an endoscope. The operation invalidating device begins operating automatically after a lapse of a predetermined time from actuation of a power source or after a lapse of a predetermined time from operation of a switch or key.

10 Claims, 12 Drawing Sheets

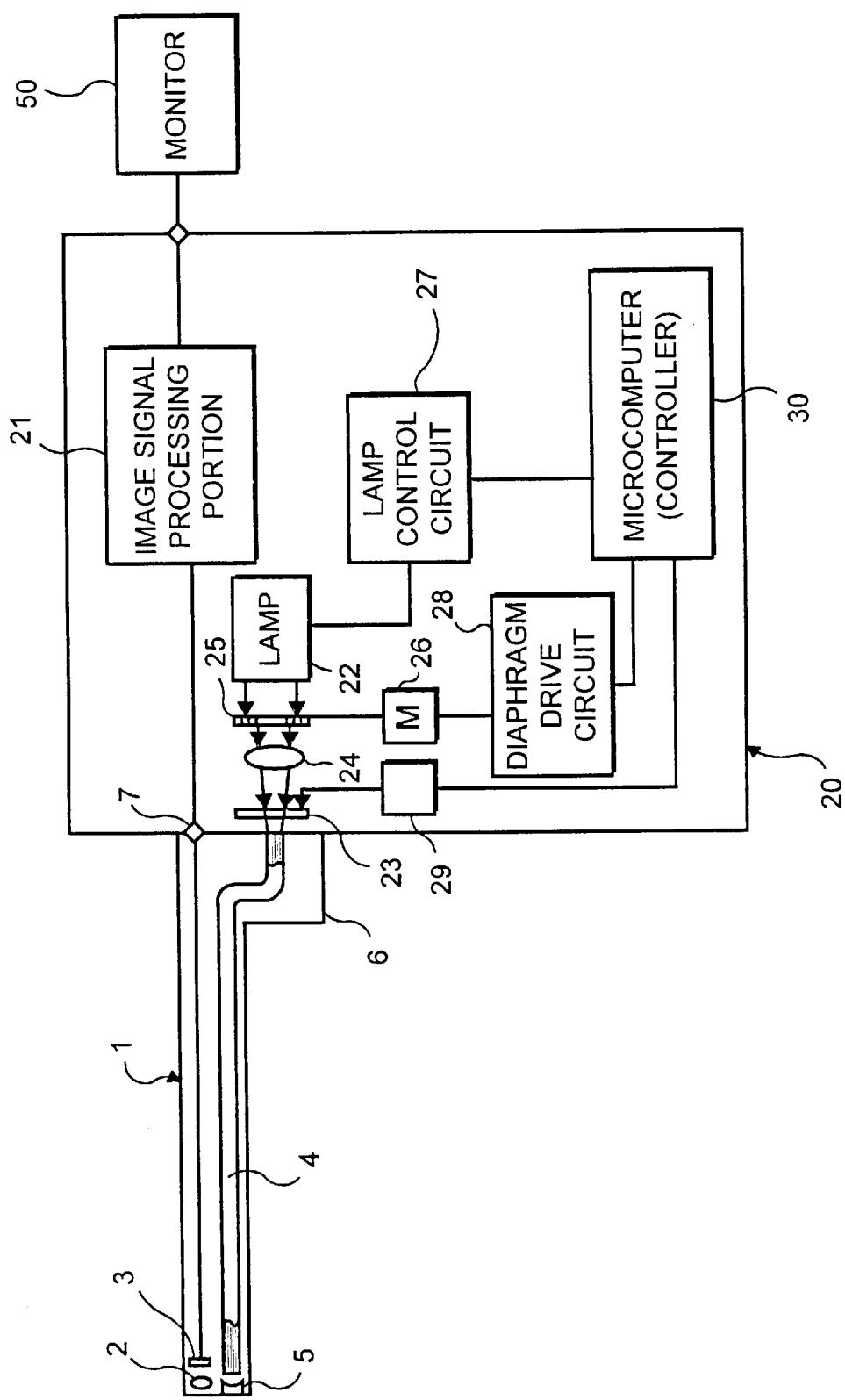
F I G. 2

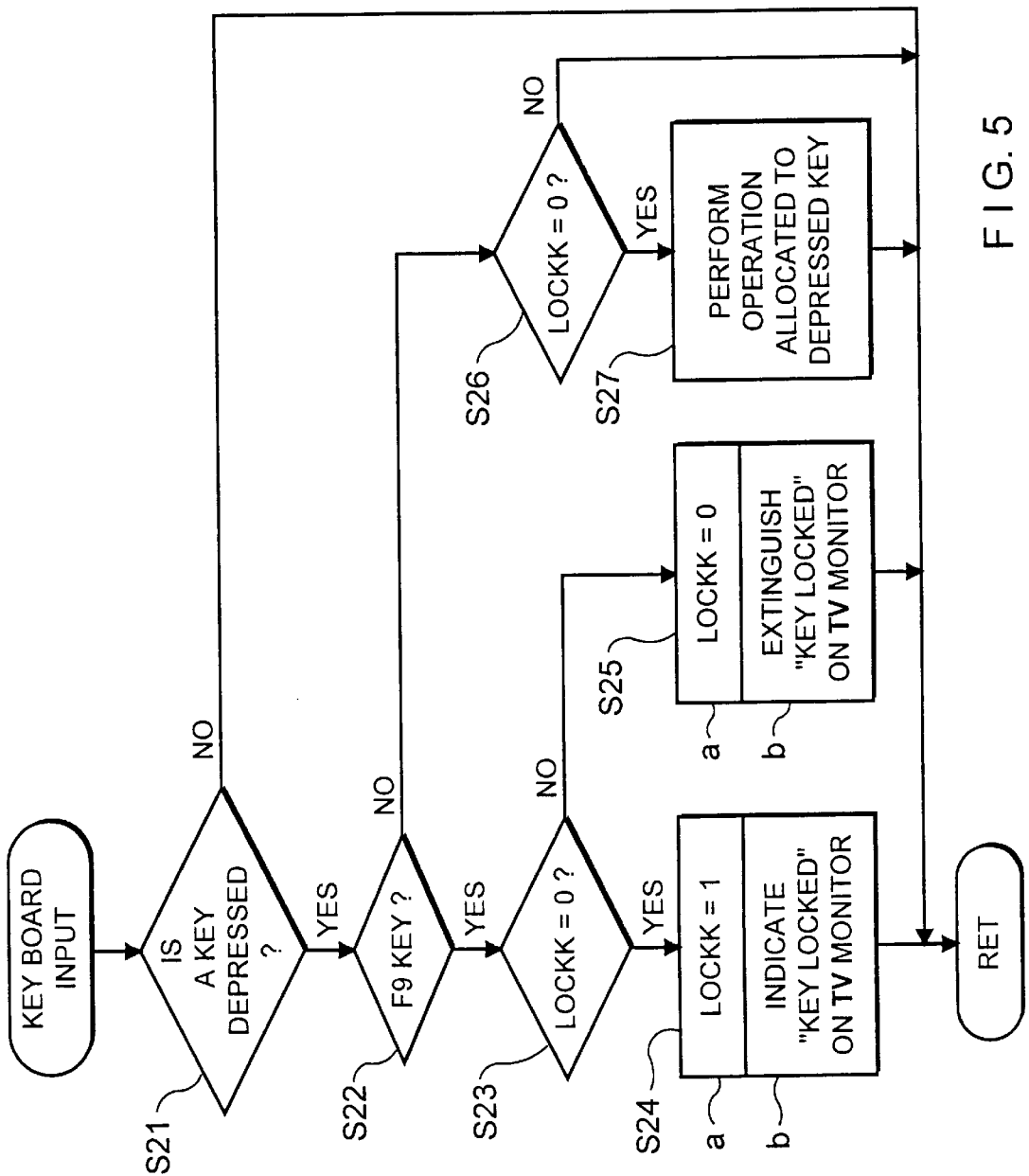
F I G. 5

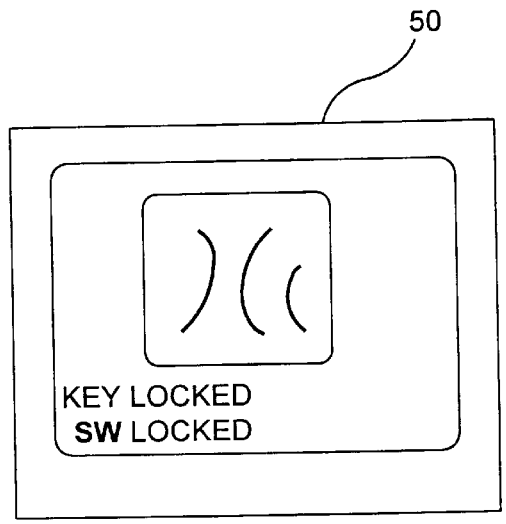
F I G. 7
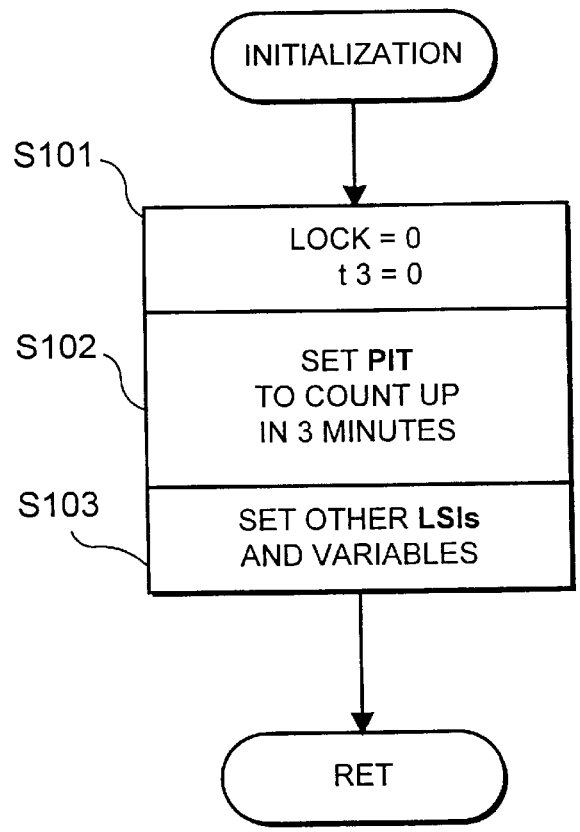
F I G. 8

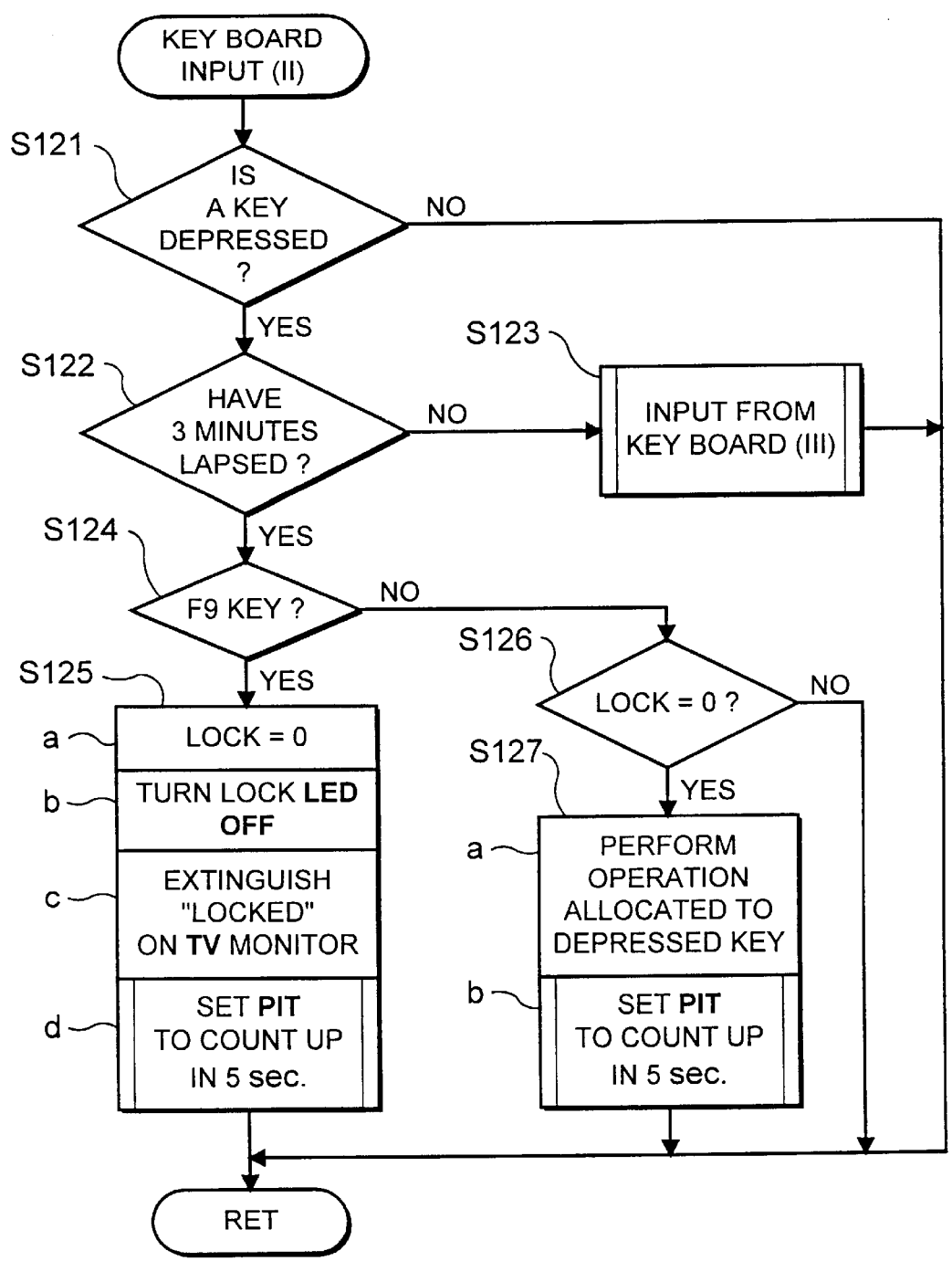
F I G. 10

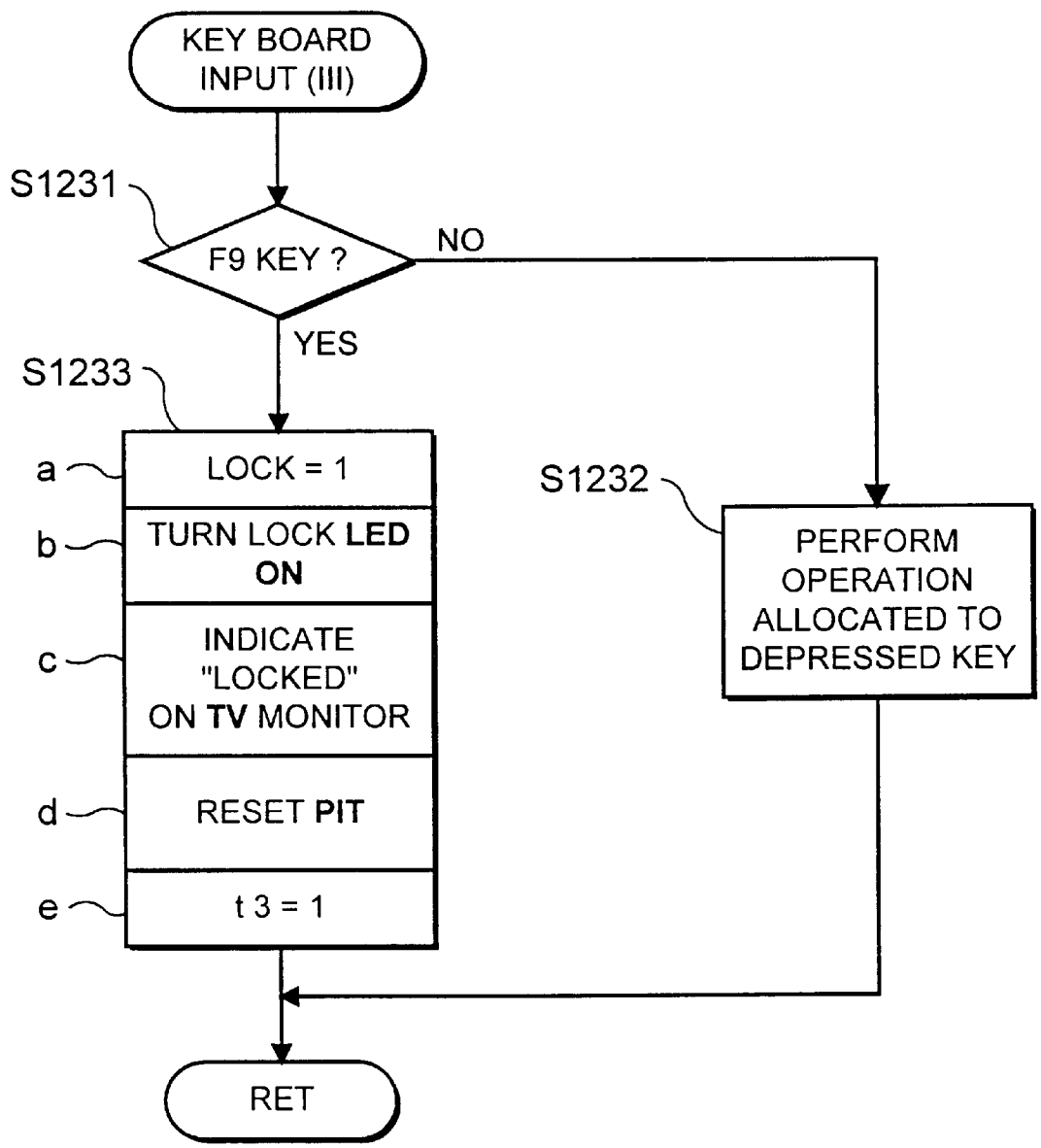
F I G. 11

ENDOSCOPE SYSTEM WITH OPERATION INVALIDATING DEVICE

BACKGROUND OF THE INVENTION

1. Field of the Invention

The present invention relates to an endoscope system having a switch or key which is adapted to control the operation of an instrument connected to an endoscope.

2. Description of the Related Art

A key board or the like, connected to an operation panel of a video processor for an electronic endoscope system or a video processor is usually provided with a switch or key, etc., to control the operation of a device or instrument connected to the endoscope.

In many cases, the switch or key is set in an appropriate state immediately after the power source of the video processor is turned ON, and the appropriate state is kept until the examination or inspection using the endoscope (endoscope inspection) is completed.

However, if an operator accidentally touches the switch or key during the inspection, the initial state is changed, so that, for example, an air supply pump is stopped or the state of an image of an object to be viewed through the endoscope, displayed on a monitor is changed. Consequently, a re-adjustment or re-setting of the image state is needed, thus resulting in no smooth endoscope inspection.

SUMMARY OF THE INVENTION

It is an object of the present invention to provide an endoscope system in which the state which has been appropriately set by the switch or key, etc., is kept even if an operator accidentally touches the key or switch, so that a smooth inspection using the endoscope can be carried out.

To achieve the object mentioned above, according to the present invention, there is provided an endoscope system comprising an operation invalidating means for invalidating the operation of a switch or key which is actuated to control the operation of a device connected to an endoscope.

In an embodiment of the invention, a plurality of keys or switches are provided. The operation invalidating means invalidates the operation of one or some of the keys or switches. The operation invalidating means can be comprised of a key or switch juxtaposed with the keys or switches.

Preferably, the operation invalidating means operates in association with the operation of a power source for the device on which the key or switch is provided, so that the operation invalidation device begins operating automatically after the lapse of a predetermined time from the operation of the power source.

The present disclosure relates to subject matter contained in Japanese Patent Application No. 08-50225 (filed on Mar., 7, 1996) which is expressly incorporated herein by reference in its entiretie.

BRIEF DESCRIPTION OF THE DRAWINGS

The invention will be discussed below in detail with reference to the accompanying drawings, in which;

FIG. 2 is a schematic view of an endoscope system according to an embodiment of the present invention;

FIGS. 4 through 6 are flow charts of a control operation according to a first embodiment of the present invention;

FIG. 7 is a front elevational view of a TV monitor according to a first embodiment of the present invention; and, FIGS. 8 through 13 are flow charts of a control operation according to a second embodiment of the present invention.

DESCRIPTION OF THE PREFERRED EMBODIMENT

Figure 1:
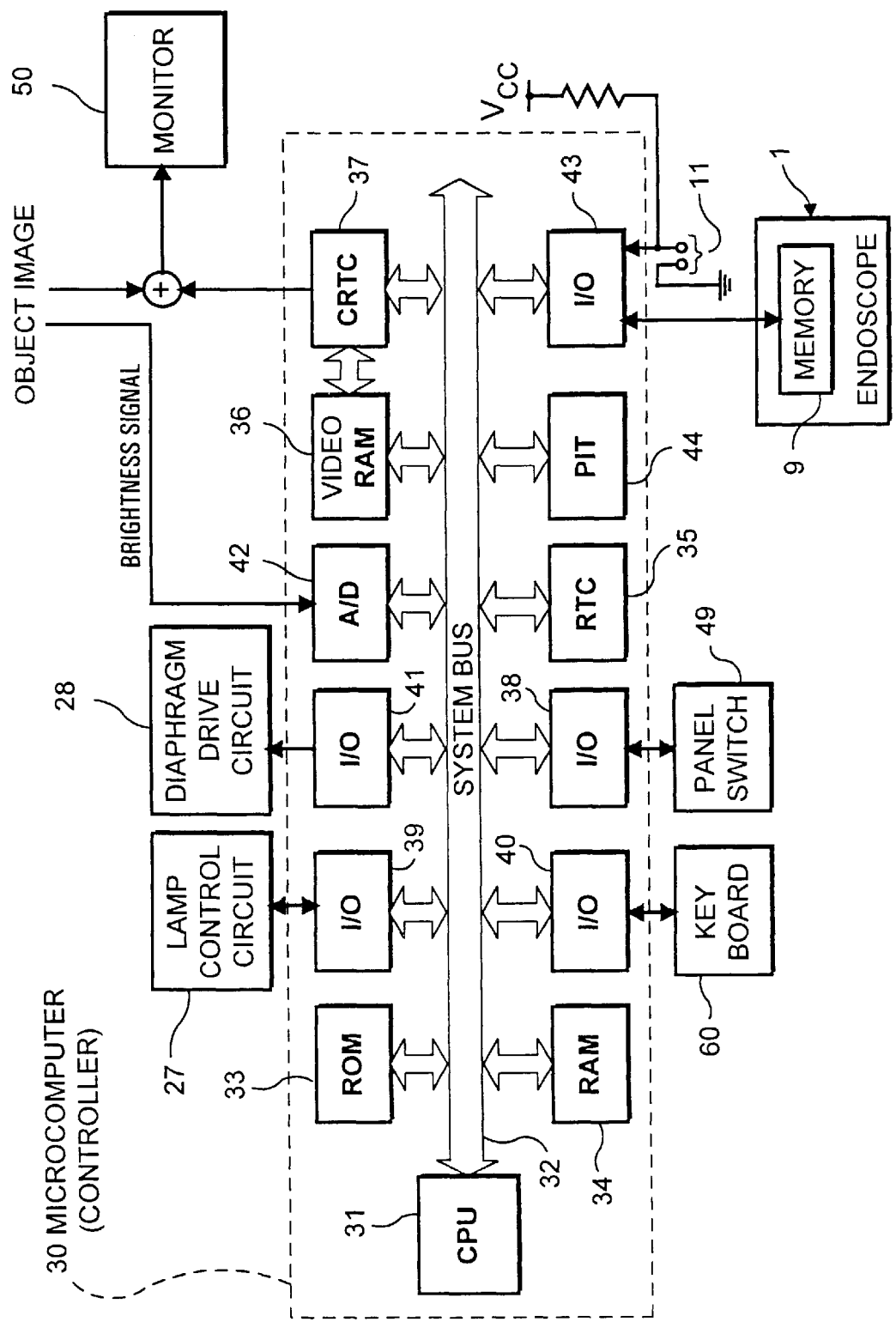
FIG. 1 is a block diagram of a controller (microcomputer) and its peripheral portion, according to the present invention.

Looking at FIG. 2 which shows a whole structure of an electronic endoscope 1 and a video processor 20 which also serves as a power source device, the electronic endoscope 1 is provided, on the front end of the insertion portion thereof, with a solid-state image pickup device 3 made of, for example, a charge-coupled device (CCD), located at an image forming position in which an object image is formed by an objective lens 2. An illumination lens 5 is opposed to an emission end of an illumination light guide fiber bundle 4 to illuminate the object with the illumination light whose emission angle (orientation angle) is increased by the illumination lens 5.

The electronic endoscope 1 is provided with a connector portion 6 which is detachably connected to the video processor 20 and which contains therein an electrical connector 7 adapted to connect signal lines transmitting signals input from or supplied to the solid-state image pickup device 3 to the video processor 20 and an input terminal of the light guide fiber bundle 4.

The video processor is provided therein with an image signal processing portion 21 to process an image signal supplied from the solid-state image pickup device 3, and a light source lamp 22 which emits the illumination light to be supplied to the light guide fiber bundle 4. The TV monitor 50 is connected to the output terminal of the image signal processing portion 21, so that the object image to be inspected by the endoscope is indicated on the TV monitor 50.

There is a condenser lens 24 between the input terminal of the light guide fiber bundle 4 and the light source lamp 22 to converge the illumination light emitted from the lamp 22 onto the input end of the light guide fiber bundle 4.

A movable diaphragm 25 is provided between the lamp 22 and the condenser lens 24 to vary the amount of the bundle of illumination light to enter the light guide fiber bundle 4 by controlling (or partly intercepting) the cross area of the illumination light path. The movable diaphragm 25 is driven by a stepping motor 26.

A rotatable RGB filter 23 which is rotated at a constant speed is provided with three filters, i.e., a red (R) filter, a green (G) filter, and a blue (B) filter which are successively inserted in the illumination light path to successively pick up the R, G, and B image elements.

A lamp control circuit 27 which drives the light source (lamp) 22, a diaphragm drive circuit 28 which drives the movable diaphragm 25, and a filter drive circuit 29 which drives the RGB filter 23 are controlled by a microcomputer (controller) 30 provided in the video processor 20.

FIG. 1 shows a microcomputer 30 and the peripheral elements thereof. The microcomputer 30 is provided with a system bus 32 connected to the central processing unit (CPU) 31 to perform an arithmetic operation. In the microcomputer 30, a read-only memory (ROM) 33 having a predetermined program stored therein, a random access memory (RAM) 34, and a real time clock (RTC) 35, etc., are connected to the system bus 32.

Letter data for indication stored in the video random access memory (video RAM) 36 and image data supplied from the image signal processing portion 21 are combined and are output to the TV monitor 50 through the CRT controller (ERTC) 37 connected to the system bus 32.

A panel switch 49 of the video processor 20, a lamp control circuit 27 which controls the lamp 22, and an external key board 60 are connected to the system bus 32 through input/output ports 38, 39 and 40, respectively.

For example, patients' names are input using the key board 60 having a number of input keys. For instance, if an f9 key (ninth function key) is depressed, the key board is brought into an input lock state in which the microcomputer 30 does not permit an operator to have an access through the key of the key board 60 and hence, and hence, all the function keys other than the f9 key are invalidated. Consequently, the previously set state does not change. If the f9 key is depressed again, the input lock state is released, so that the key operation can be carried out.

Figure 3:
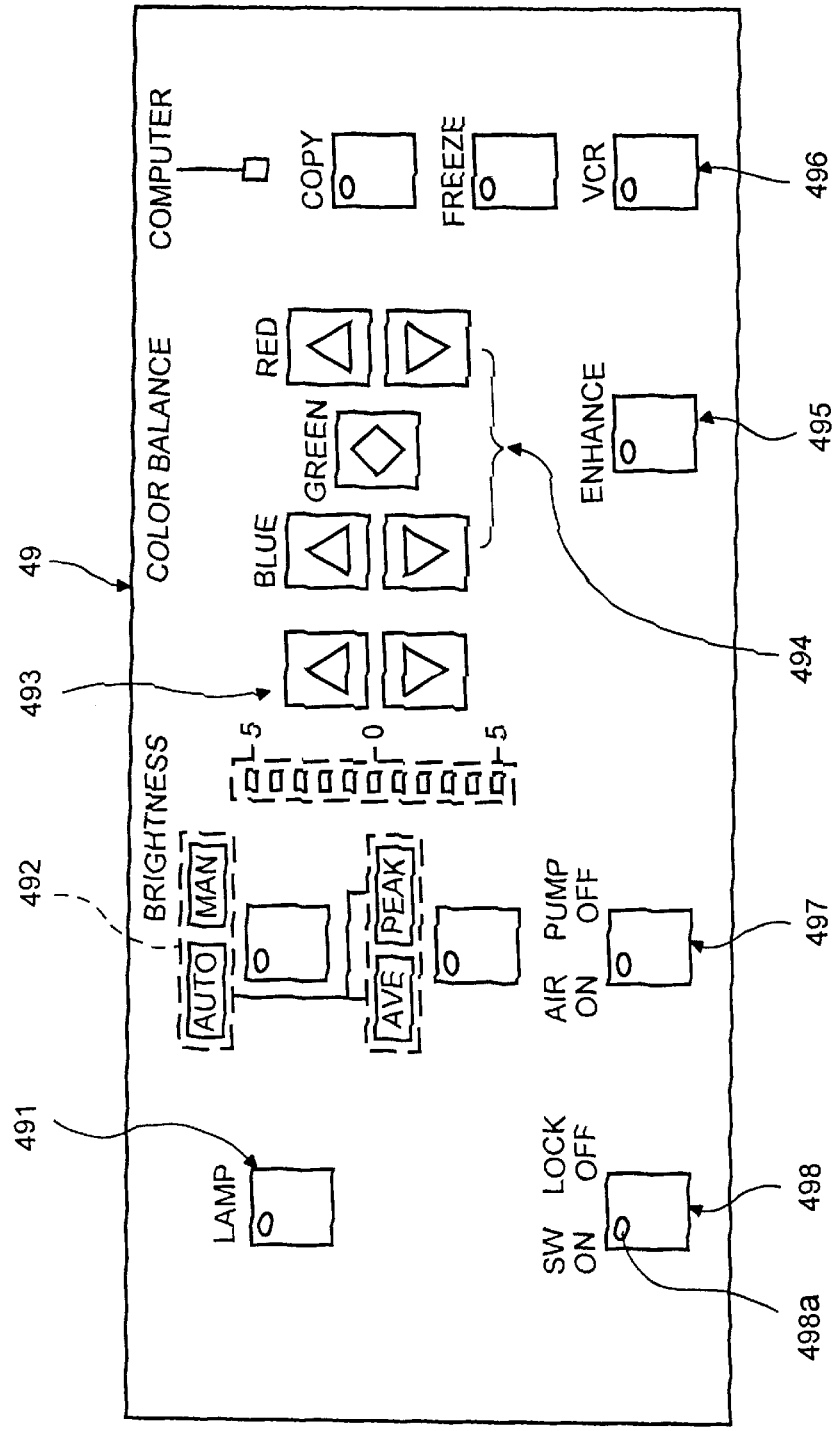
FIG. 3 is a front elevational view of a panel switch according to the present invention.

The panel switch 49 is provided with various operation switches, as shown in FIG. 3. A power switch (not shown) is provided in a portion other than the panel switch 49. In FIG. 3, the reference numeral 491 designates the lamp switch which is actuated to turn the lamp ON or OFF, 492 the switch which is actuated to select the control method for controlling the brightness of the illumination light to be made incident upon the light guide fiber bundle 4, and 493 the brightness control switch which is actuated to manually set the brightness of the illumination light to be made incident upon the light guide fiber bundle 4, respectively.

The reference numeral 494 designates the color tone control switch which is actuated to adjust the color tone of the object image indicated on the monitor TV 50, and 495 designates the enhancement switch which is actuated to emphasize or not to emphasize the outline of the object image indicated in the monitor TV 50.

The reference numeral 496 designates the external device control switch which is actuated to obtain a hard copy of the object image displayed in the monitor TV 50, or stop the movement of the object image, or record the object image onto a video tape, etc., 497 the pump switch which is actuated to turn the air supply pump ON or OFF, respectively.

The reference numeral 498 connotes the input lock switch which is actuated to lock the state selected by the lamp switch 491, the tone control switch 494, or the pump switch 497.

The input lock switch 498 is turned ON or OFF by each depression. When the input lock switch is ON, the lamp switch 491, the tone control switch 494 and the pump switch 497 are invalidated, that is, if the input lock switch is ON, the lamp switch 491, the tone control switch 494 or the pump switch 497 is depressed, the depression is ineffective and hence the previously set state is maintained.

When the input lock switch 498 which is in the ON state is depressed, the switch is turned OFF, and hence the lock is released. Consequently, the operation of the lamp switch 491, the tone control switch 494 or the pump switch 497 is made effective.

Turning to FIG. 1, when the connector portion 6 of the electronic endoscope 1 is connected to the light source/video processor 20, the memory 9 provided in the endoscope 1 is connected to the microcomputer 30 through the I/O port 43. The memory 9 stores therein data inherent to the endoscope 1, such as the kind of the endoscope, etc.

Moreover, a dip switch 11 connected to the I/O port 43 is manually turned ON or OFF to switch the input terminal of the I/O port 43 between a high level (H) or low level (L).

The reference numeral 44 designates the programmable interval timer (PIT) connected to the system bus 32, in which the counter output of the PIT 44 is connected to the interruption terminal of the CPU 31, so that when the counter value set in the counter of the PIT 44 is varied, the time interval of the interruption operation is varied. Note that the control signal output from the microcomputer 30 is sent also to the image signal processing portion 21 and the pump drive circuit (not shown), etc.

Figure 4:
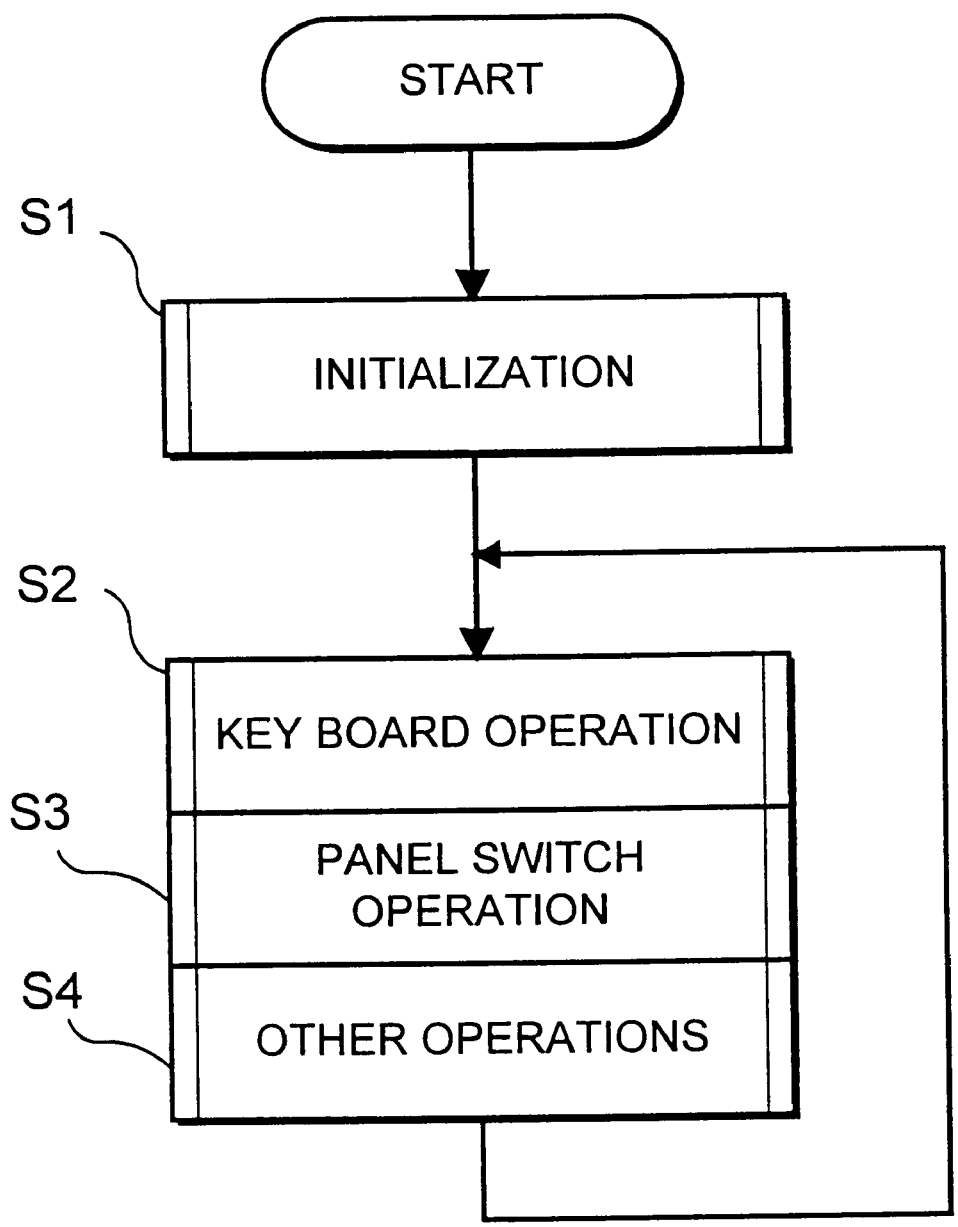
Figure 6:
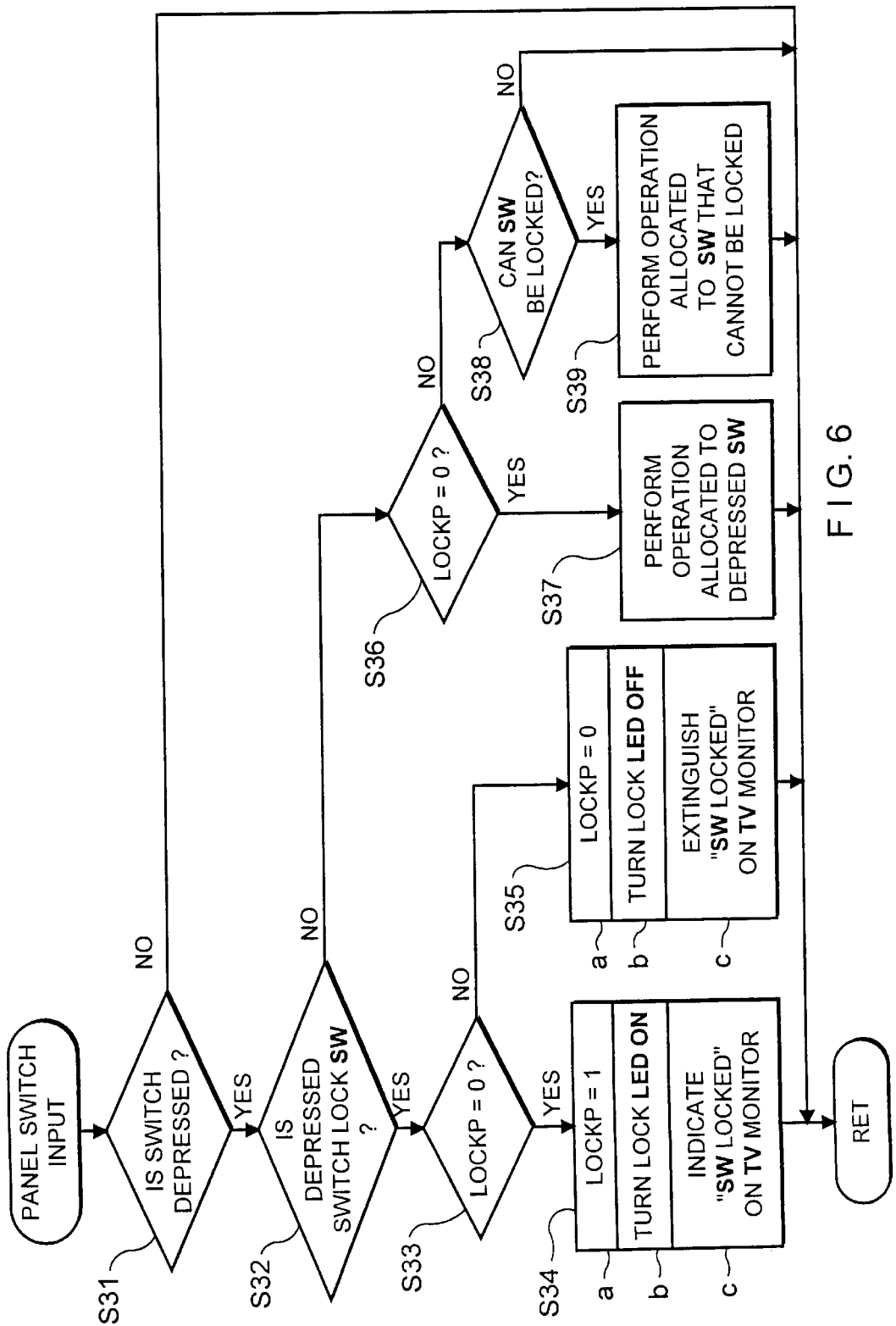

FIGS. 4 through 6 show the content of the program performed in the microcomputer 30 according to a first embodiment of the present invention. In the drawings, S represents the operation step.

In FIG. 4 which shows the main program, the predetermined initialization is carried out at step S1, and thereafter, the input operation from the key board 60 (S2), the operation by the panel switch 49 (S3), and other operations (S4) are successively and repeatedly carried out.

In FIG. 5 which shows the operation from the key board 60, whether or not any one of the keys of the key board 60 is depressed is checked at step S21. If a key is depressed, whether or not the key is the f9 key is checked at step S22. If no key is depressed at step S21, the key board operation at step S2 ends and the control proceeds to the panel switch operation (step S3).

If the f9 key is depressed at step S22, whether or not the variable "Lockk" is 0 is checked (step S23). If the variable "Lockk" is 0, the variable is changed to 1 and "Key Locked" is indicated in the monitor TV 50 at step S24 (a, b, as can be seen in FIG. 7.

If the variable "lockk" is not 0 at step S23 (i.e., "lockk" is 1), the variable is changed to 0, and "Key Locked" on the monitor TV 50 disappears at step S25 (a, b).

If the key depressed is not the f9 key at step S22, whether or not the variable "lockk" is 0 is checked (step S26). If the variable "lockk" is 0, the operation assigned for the depressed key is performed (step S27). If the variable "lockk" is not 0, the key board operation at step S2 ends and the control proceeds to the panel switch operation at step S3.

FIG. 6 shows the panel switch operation. Whether or not any one of the switches of the panel switch 49 is depressed is checked at step S31. If a switch is depressed, whether or not the switch is the input lock switch 498 is checked at step S32. If no switch is depressed at step S31, the switch panel operation at step S3 ends and the control proceeds to other operations at step S4.

If the input lock switch 498 is depressed at step S32, whether or not the variable "lockp" is 0 is checked at step S33. If the variable "lockp" is 0, the variable is changed to 1, and thereafter, the lock LED (light emitting diode) 498a provided on the input lock switch 498 is lit and the "SW Locked" is indicated in the monitor TV 50, at steps S34 (a, b, c), as can be seen in FIG. 7.

If the variable "lockp" is not 0 at step S33 (i.e., if the variable "lockp" is 1), the variable is changed to 0 and thereafter, the lock LED 498a is turned OFF and "SW Locked" is extinguished in the monitor TV 50 at step S35 (a, b, c).

If the switch depressed is not the input lock switch 498 at step S32, whether or not the variable "lockp" is 0 is checked (step S36). If the variable "lockp" is 0, the operation allocated to the depressed key is performed (step S37). If the variable "lockp" is not 0, whether the depressed switch is a switch which can be locked by the input lock switch 498 is checked at step S38.

If the depressed switch is not the switch that cannot be locked, the operation allocated to that switch is carried out (step S39). If the depressed switch is a switch that can be locked, the panel switch operation ends and the control proceeds to other operations at step S4.

FIGS. 8 through 13 show the program performed in the microcomputer 30 according to a second embodiment of the present invention. In this embodiment, the panel switch 49 and the key board 60 are automatically brought into the locked position as in the first embodiment three minutes after the operation of the power source of the light source/video processor 20. The three minutes can be replaced with 1.5 minutes or 2 minutes or 4 minutes, etc.

In general, since an operator carries out first the setting operation of the light source/video processor 20 immediately after the power source is turned ON, there is no problem with the presence of the space of time of 3 or less or more minutes.

In order to make it possible to intentionally input from the key board or the panel switch after the automatic transfer to the input lock position, if the f9 key of the key board 60 or the input lock switch 498 of the panel switch 49 is depressed, the locked state is released for a predetermined short period of time (e.g., 5 seconds), so that the operator can actuate the key or switch.

In the second embodiment, the main program shown in FIG. 4 is the same as that of the first embodiment. In this connection, in the second embodiment, the program shown in FIG. 8 starts in association with the operation of the power source of the light source/video processor 20.

In this program, the content of the initialization at step S1 in FIG. 4 is shown in FIG. 8. First, the variable "lock" and the variable t3 to detect the lapse of three minutes are set 0, (step S101), thereafter, the interval timer 44 is set such that the count is up in 3 minutes. Thereafter, the interruption program shown in FIG. 9 starts in three minutes (step S102). Thereafter, other various LSIs or variables are appropriately set at step S103, and the control ends.

Figure 9:
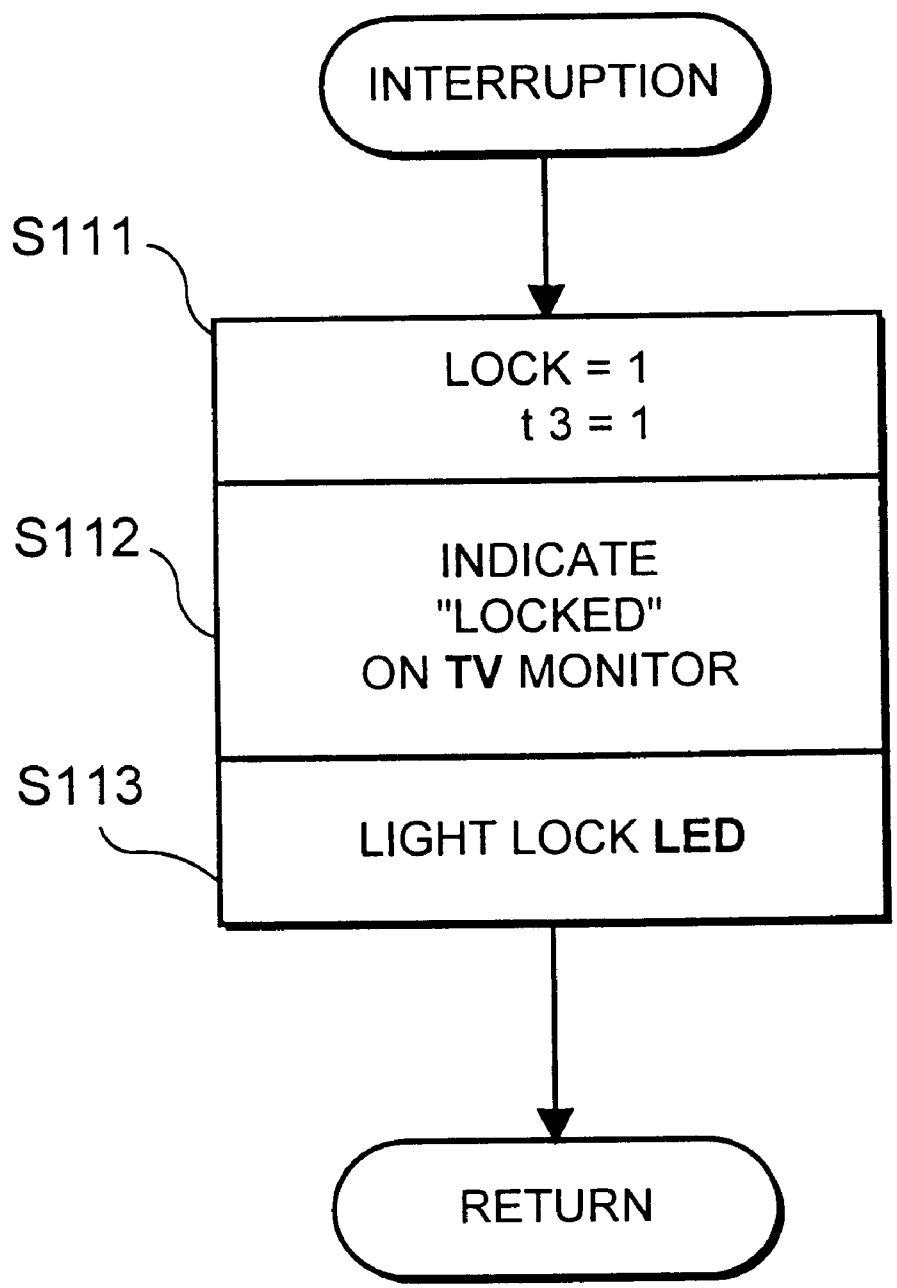

In the interruption program shown in FIG. 9, the variable "lock" and the variable t3 are set 1 (step S111) and "Locked" is indicated in the monitor TV 50 (step S112). Thereafter, the lock LED 498a is lit and the control ends (step S113). The interruption program begins when the interval timer 44 counts up.

FIG. 10 shows the content of the key board operation. Whether or not any one of the keys of the key board 60 is depressed is checked at step S121. If no key is depressed, the key board operation at step S2 ends and the control proceeds to the panel switch operation at step S3.

If a key is depressed at step S121, whether or not three minutes have lapsed after the main switch has been turned ON, i.e., whether or not t3=1 is checked at step S122. If three minutes have not yet lapsed, the key board operation shown in FIG. 11 at step 3 is carried out (step S123).

Namely, whether or not the depressed key is the f9 key is checked (step S1231). If the depressed key is not the f9 key, the operation allocated to the depressed key is carried out at step S1232, and the control proceeds to the panel switch operation at step S3.

If the f9 key is depressed at step S1231, the variable "lock" is set 1 and the lock LED 498a is lit, so that "Locked" is indicated in the monitor TV 50. Thereafter, the interval timer 44 is reset (so as not to proceed with the interruption operation shown in FIG. 9 after the lapse of three minutes), and the variable t3 is set 1 at step 1232 (a, b, c, d, e).

Thereafter, the control proceeds to the panel switch operation at step S3.

If more than three minutes have lapsed at step S122, whether or not the f9 key is depressed is checked at step S124.

If the f9 key is depressed, the variable "lock" is set 0 and the lock LED 498a is extinguished, so that "Locked" in the monitor TV 50 disappears. Thereafter, the interval timer 44 is set to count up in 5 seconds. Thus, the interruption program shown in FIG. 9 starts in 5 seconds at step S125 (a, b, c, d).

If the depressed key is not the f9 key at step S124, whether or not the variable "lock" is 0 is checked at step S126. If the variable "lock" is 0, the operation allocated to the depressed key is carried out and thereafter, the interval timer 44 is set to count up in 5 seconds, so that the interruption program shown in FIG. 9 begins in 5 seconds at step S127 (a, b). If the variable "lock" is not 0, the key board operation ends and the control proceeds to the subsequent panel switch operation.

Figure 12:
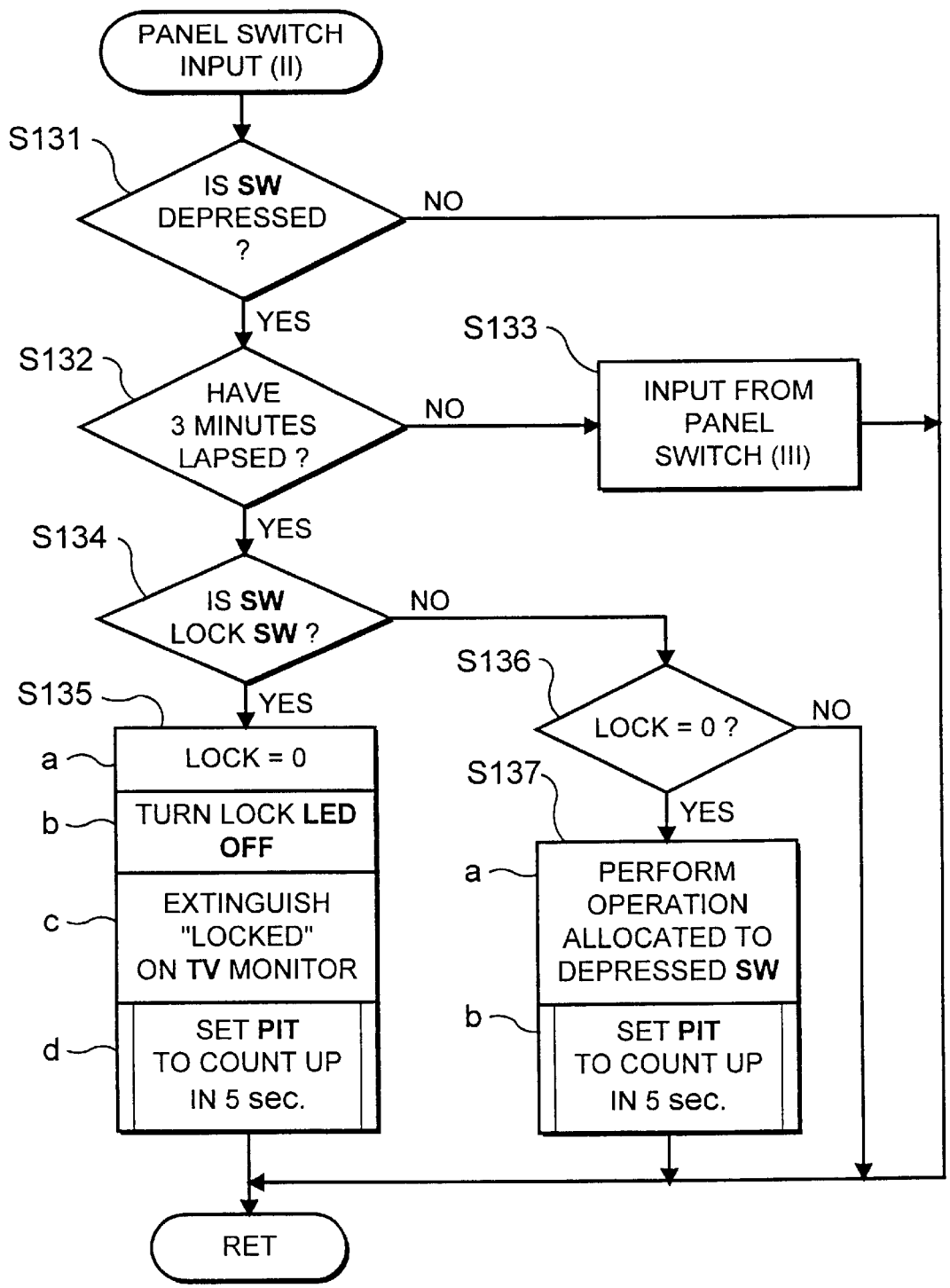

FIG. 12 shows the content of the panel switch operation at step S3 according to the second embodiment. First, whether or not any one of the switches of the panel switch 49 is depressed is checked at step S131.

Figure 13:
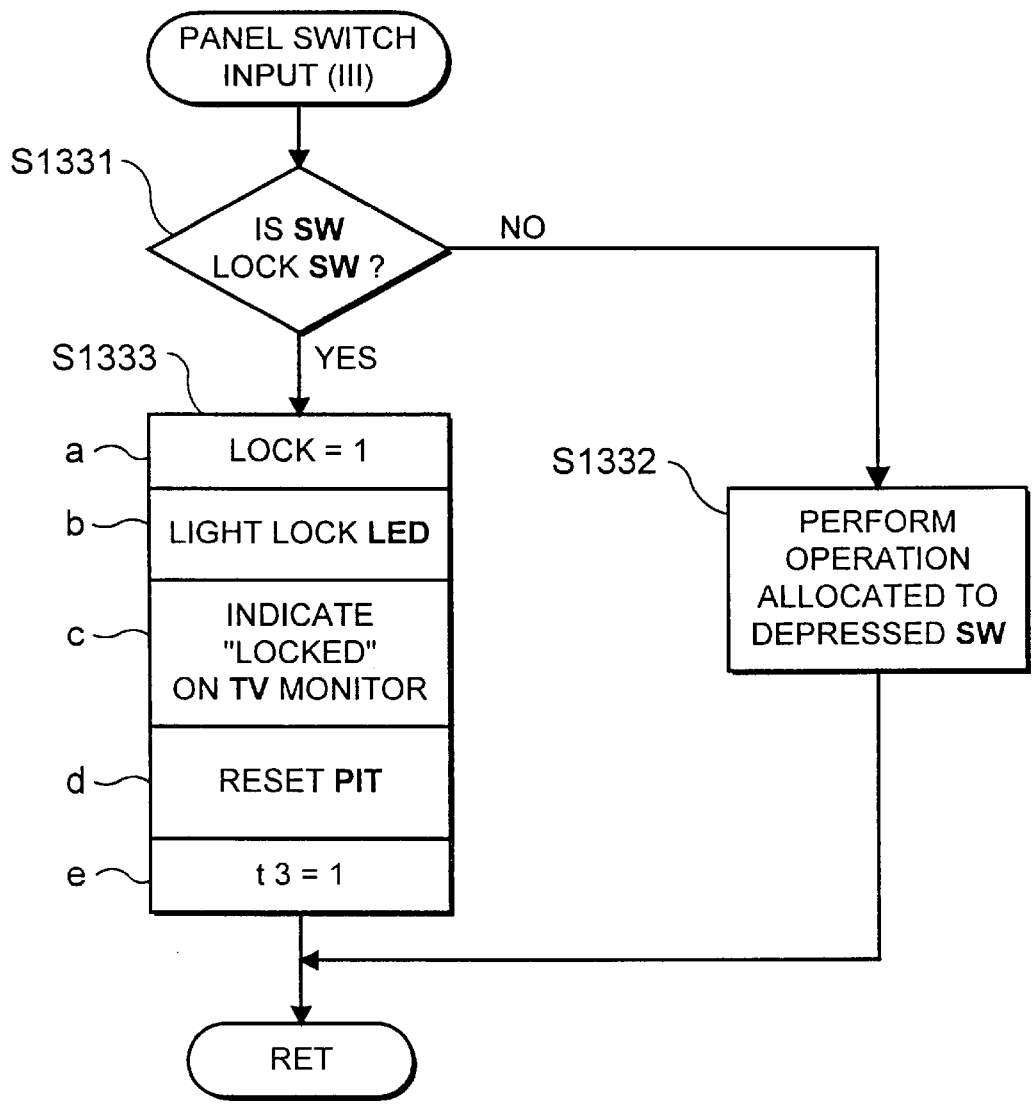

If no switch is depressed, the panel switch operation at step S3 ends and the control proceeds to the subsequent other operation at step S4. If a switch is turned ON at step S131, whether or not three minutes have lapsed after the main switch has been turned ON, i.e., whether or not t3=1 is checked at step S132. If three minutes have not yet lapsed, the operation shown in FIG. 13 is carried out (step S133).

Namely, whether or not the depressed key is the input lock switch 498 is checked (step S1331). If the depressed switch is not the input lock switch 498, the operation allocated to the depressed switch is carried out at step S1332, and the control proceeds to the subsequent operation at step S4.

If the input lock switch 498 is depressed at step S1331, the variable "lock" is set 1 and the lock LED 498a is lit, so that "Locked" is indicated in the monitor TV 50. Thereafter, the interval timer 44 is reset (so as not to proceed with the interruption operation shown in FIG. 9 after the lapse of three minutes), and the variable t3 is set 1 at step 1332 (a, b, c, d, e). Thereafter, the control proceeds to the other operation at step S4.

If more than three minutes have lapsed at step S132, whether or not the input lock switch 498 is depressed is checked at step S134.

If the input lock switch 498 is depressed, the variable "lock" is set 0 and the lock LED 498a is turned OFF to extinguish the indicia of "Locked" in the monitor TV 50. Thereafter, the interval timer 44 is set to count up in 5 seconds. Thus, the interruption program shown in FIG. 9 begins in 5 seconds at step S135 (a, b, c, d).

If the depressed switch is not the input lock switch 498 at step S134, whether or not the variable "lock" is 0 is checked at step S136. If the variable "lock" is 0, the operation allocated to the depressed switch is carried out and thereafter, the interval timer 44 is set to count up in 5 seconds, so that the interruption program shown in FIG. 9 begins in 5 seconds at step S137 (a, b). If the variable "lock" is not 0, the panel switch operation at step S3 ends and the control proceeds to the subsequent operation.

The present invention is not limited to the illustrated embodiments, and can be applied to any types of key or switch to be locked. Moreover, the present invention can be applied to an endoscope system using a fiber scope or a hard endoscope, etc., in which the object image is transmitted through an image guide fiber or a relay lens system.

As can be understood from the above discussion, according to the present invention, since the provision is made of an operation invalidating means for invalidating the operation of a switch or key which is actuated to control the operation of a device or instrument connected to the endoscope, the state which has been set appropriately by the switch or key can be maintained if the switch or key is accidentally touched, thus resulting in a smooth inspection through the endoscope.

Moreover, if the operation invalidating means operates in association with the operation of the power source for the device in which the switch or key is provided, namely if the operation invalidating means becomes effective automatically, after the lapse of a predetermined time from the commencement of the power supply, no special operation for the operation invalidating means is conveniently necessary.

What is claimed is:

1. An endoscope system, comprising:

an external device connected to an endoscope;

switches or keys connected to said external device which are actuated to control an operation of said external device; and, an operation invalidating device to invalidate said switches or keys;

wherein said operation invalidating device operates in association with an actuation of a power source of said external device or in association with an operation of at least one of said switches or keys provided on said external device, so that said operation invalidating device begins operating automatically after the lapse of a predetermined time (i) from said actuation of said power source or (ii) from said operation of said at least one of said switches or keys.

2. An endoscope system according to claim 1, wherein said operation invalidating device invalidates the operation of a part of said keys or switches.

3. An endoscope system according to claim 1, wherein said operation invalidating device is comprised of a key or switch juxtaposed with said keys or switches.

4. An endoscope system according to claim 1, wherein said switches or keys are comprised of a keyboard.

5. An endoscope system according to claim 1, wherein said switches or keys are comprised of a panel switch.

6. An endoscope system according to claim 1, wherein said external device is comprised of a computer which memorizes data to actuate another external device and said data is selected, changed, inputted or set by said switches or keys.

7. An endoscope system according to claim 1, wherein said operation invalidating device invalidates an operation of said switches or keys to select, change, input or set said data.

8. An endoscope system according to claim 1, wherein said operation invalidating device has a invalidating switch juxtaposed with said keys or switches, wherein said operation invalidating device permits said operation of said switches or keys when said invalidating switch is turned on, and said operation invalidating device invalidates said operation of said switches or keys when said invalidating switch is turned off.

9. An endoscope system according to claim 1, further comprising an indicator which indicates when said operation invalidating device invalidates an operation of said switches or keys.

10. An endoscope operating system according to claim 1, wherein said predetermined time measured from said actuation of said power source is longer than said predetermined time measured from said operation of said at least one of said switches or keys.

* * * * *